Nov. 25, 1952 F. MEILLAND Plant Pat. 1,149
ROSE PLANT
Filed Sept. 17, 1951
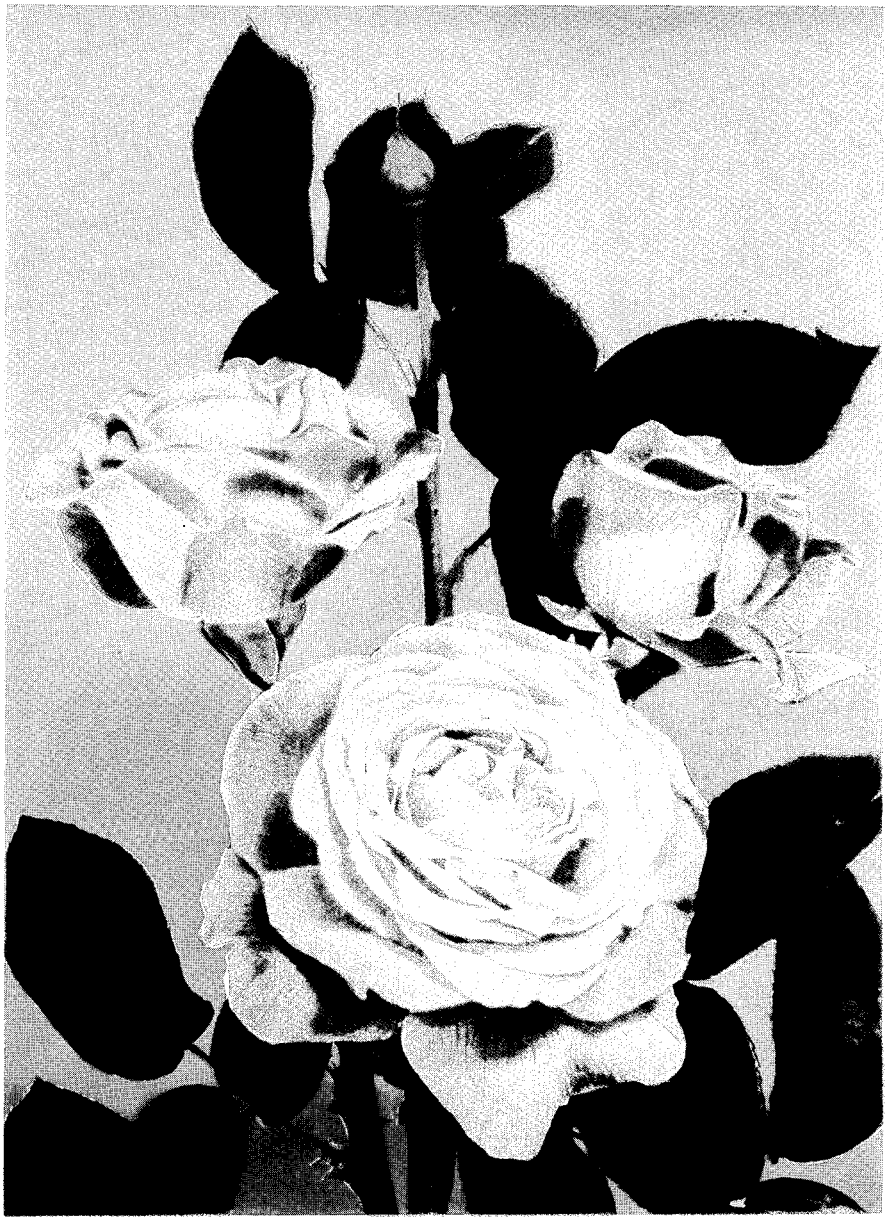
Inventor.
Francis Meilland
By: Robert Cobb
Attorneys.

Patented Nov. 25, 1952

Plant Pat. 1,149

UNITED STATES PATENT OFFICE 1,149

ROSE PLANT

Francis Meilland, Cap Azura, Cap d'Antibes, Alps Maritime, France, assignor to The Conard-Pyle Company, West Grove, Pa., a corporation of Pennsylvania Application September 17, 1951, Serial No. 246,932
In France October 16, 1950, 1 Claim. (Cl. 47—61)

The present invention relates to a new and distinct variety of rose plant of the hybrid tea class, originated by me by crossing the variety "Peace" (Plant Patent No. 591) × the variety "Signora" (Plant Patent No. 201).

As the result of this cross, I have produced a new variety that is distinctly different from its parents, as well as from any other known variety of this class, although it bears a considerable resemblance to "Peace" except for the color of its flowers which is entirely different from this parent, and from any other seedling thereof commercially known to date.

From the variety "Peace," my new variety has inherited great vigor of growth, with consequent production of heavy canes; foliage that closely resembles that of "Peace"; and large size of its blooms, with many petals. In respect to the color of its blooms, my new variety is distinctly different from "Peace" by being an even, smooth and clear pink color. In addition, the blooms of the new variety are much more fragrant than those of either parent.

Asexual reproduction of the new variety by budding at Tassin-les-Lyon, France, and at West Grove, Pennsylvania, U. S. A., shows that the foregoing characteristics and distinctions come true to form and are established and transmitted through succeeding propagations.

The accompanying drawing shows specimens of the new variety, with the flowers and foliage in different stages of development.

The following is a detailed description of the new variety, with color terminology in accordance with Ridgway's Color Standards and Nomenclature, except where general color terms of ordinary dictionary significance are obvious:

Type: Hardy; bush; outdoor; seedling; for cut flowers and for garden decoration.
Class: Hybrid tea.
Parentage: Seedling.
*Seed Parent.*—"Peace."
*Pollen parent.*—"Signora."
Propagation: Holds its distinguishing characteristics through succeeding propagations by budding.

*Flower*

Locality where grown and observed: West Grove, Pennsylvania, U. S. A.
Flowers borne: Singly to stem; on strong, medium length stems.
Quantity of bloom: Free, outdoors.
Continuity: Continuous.
Fragrance: Strong; tea.

Bud:
*Peduncle.*—Medium length; medium heavy; erect; stiff; moderately rough; medium number of red prickles. Color—Yellowish Oil Green, Plate V, often tinged with Pompeian Red, Plate XIII.
*Before calyx breaks.* — Size — medium. Form—medium length; pointed; ovoid; with foliaceous appendages on the surface of the bud; with slender, little cut foliaceous parts extending beyond the tip of the bud equal to ⅛ or more of its length.
*As calyx breaks.*—Color—Geranium Pink, Plate I.
*As first petal opens.* — Size — medium. Form—medium length; ovoid to globular. Color: outside—Pale Green-Yellow, Plate V, shading to Geranium Pink, Plate I, at base; light to dark Tyrian Rose, Plate XII, over most of petal surface; inside—Pale Greenish Yellow, Plate V, at base; Rose Red, Plate XII, to Tyrian Rose, Plate XII, over most of petal surface.
*Opening.*—Opens up well.
Bloom:
*Size, when fully open.*—Large; 4¼ inches to 4¾ inches, or more.
*Petalage.*—Double to very double; from 55 to 60 petals; arranged regularly.
*Form.*—High-centered at first; becoming rather cupped; petals being at first cupped inward with outer edges rolled outward; becoming later, at maturity, loosely rolled outward.
Petals: Medium thick; with inside satiny and outside shiny.
*Shape.—Outer*—obovate; usually with apex coming to a small point. Intermediate—usually with apex coming to a small point. Inner—usually with apex coming to a small point.
*Color.*—Colors may be modified by being White to Martius Yellow, Plate IV, at base of outside petal surface and by being White to Pinard Yellow, Plate IV, at base of inside petal; also colors may be modified by being shaded with other colors.

This description of a newly opened flower was made from a rose grown outdoors in the month of October, at West Grove, Pennsylvania:

*Color.*—Outer petal: outside surface—Light Rosolane Purple, Plate XXVI, to Rose Color, Plate XII; inside surface—Tyrian Rose, Plate XII, to Rose Red, Plate XII.

Intermediate petal: outside surface—Deep Rose Pink, Plate XII; inside surface—Tyrian Rose, Plate XII, to light Tyrian Rose, Plate XII. Inner petal: outside surface—Deep Rose Pink, Plate XII, with shadings of Hermosa Pink, Plate I; inside surface—Tyrian Rose, Plate XII, to light Tyrian Rose, Plate XII.

This description was made from a rose that was open for three days outdoors in the month of October, at West Grove, Pennsylvania:

*Color.*—Outer petal: outside surface—Rose Pink, Plate XII, to Deep Rose Pink, Plate XII; inside surface—Tyrian Rose, Plate XII, to dark Tyrian Pink, Plate XII. Inner petal: outside surface—Rose Pink, Plate XII; inside surface—Light Tyrian Pink, Plate XII.

*General color effect.*—Newly open flower—Tyrian Rose Plate XII, to light Tyrian Rose, Plate XII, with shadings of Deep Rose Pink, Plate XII, where reverse of petals shows. Three days open—Tyrian Pink, Plate XII, at outer edges of light Tyrian Pink, Plate XII, nearer center.

*Behavior.*—Drop off cleanly.

*Flower longevity.*—Cut roses grown outdoors kept at living-room temperatures—4 to 5 days in October.

*Reproductive organs*

Stamens: Medium number; arranged regularly about pistils.

Filaments: Most with anthers of various lengths; short to medium length. Color—Old Rose, Plate XIII.

Anthers: All open at once; medium size; occasionally an anther fused with a petaloid or pistil. Color—Orange-Buff, Plate III.

Pollen: Moderate abundance. Color—Orange-Buff, Plate III.

Pistils: Medium number.

Styles: Uneven; most medium length; medium weight; bunched.

Stigma: Yellowish-white color.

Ovaries: All enclosed in calyx.

Hips: Medium length; globular; smooth; walls medium thickness. Color—Lettuce Green, Plate V.

Sepals: Permanent; medium length; spear-shaped.

Seeds: Few; medium size.

*Plant*

Foliage:

*Leaves.*—Compound of 3 to 5 leaflets; normal to abundant; medium size; leathery.

*Leaflets.*—Shape—oval with apex acute. Base—obtuse. Margin—simply serrate.

*Color.*—Mature: upper surface—Dark Cress Green, Plate XXXI; under surface—Light Cress Green, Plate XXXI. Young: upper surface—Kronberg's Green, Plate XXXI, along midrib; overlaid with Mineral Red, Plate XXVII, over most of surface; under surface—Deep Corinthian Red, Plate XXVII.

*Rachis.*—Medium weight. Upper side—grooved. Under side—moderately prickly and thorny. Under side of midribs of leaflets sparsely prickly.

*Stipules.*—Medium length; medium width; with moderately short points; turning out at an angle of less than 90°.

*Disease.*—Resistant to mildew and blackspot, as determined by comparison with other varieties of the same class grown under comparable conditions at West Grove, Pennsylvania.

Growth:

*Habit.*—Bushy; upright; branched.

*Growth.*—Vigorous.

*Canes.*—Heavy.

*Main stems.*—Color—Dark Parrot Green, Plate VI. Thorns—several; medium length; usually hooked downward; with medium length oval base. Prickles—few; color—Pompeian Red, Plate XIII. Hairs—none.

*Branches.*—Color—Calla Green, Plate V. Thorns—several; medium length; hooked downward; with medium short oval base. Prickles—few; color—Jasper Red, Plate XIII. Hairs—none.

*New shoots.*—Color—Oil Green, Plate V. Thorns—several; medium length; hooked downward; with medium short oval base. Prickles—few; color—Pompeian Red, Plate XIII. Hairs—none.

I claim:

A new and distinct variety of rose plant of the hybrid tea class, substantially as herein shown and described, characterized as to novelty by its general similarity to the variety "Peace" (Plant Patent No. 591) in respect to its great vigor, heavy canes, similar foliage, and large blooms with many petals, while dominantly differing therefrom by the even, smooth, clear pink color of its blooms, and by their relatively strong fragrance.

FRANCIS MEILLAND.

No references cited.